(12) United States Patent  (10) Patent No.: US 8,795,288 B2
Melsheimer et al.  (45) Date of Patent: Aug. 5, 2014

(54) ACCESS DEVICE

(75) Inventors: Jeffry S. Melsheimer, Springville, IN (US); Darin G. Schaeffer, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 944 days.

(21) Appl. No.: 11/874,444

(22) Filed: Oct. 18, 2007

(65) Prior Publication Data
US 2008/0109009 A1  May 8, 2008

Related U.S. Application Data

(60) Provisional application No. 60/856,149, filed on Nov. 2, 2006.

(51) Int. Cl.
*A61F 11/00* (2006.01)
(52) U.S. Cl.
USPC .......................... 606/108; 604/523; 604/528
(58) Field of Classification Search
USPC .................................. 623/1.11; 606/128, 108
See application file for complete search history.

(56) References Cited

U.S. PATENT DOCUMENTS

| 1,207,479 | A | | 12/1916 | Bisgaard |
| 3,119,392 | A | * | 1/1964 | Zeiss et al. ................... 606/127 |
| 4,568,338 | A | | 2/1986 | Todd |
| 4,643,716 | A | | 2/1987 | Drach |
| 5,487,385 | A | | 1/1996 | Avitall |
| 5,599,294 | A | | 2/1997 | Edwards et al. |
| 5,630,823 | A | * | 5/1997 | Schmitz-Rode et al. ...... 606/128 |
| 5,840,013 | A | * | 11/1998 | Lee et al. ...................... 600/114 |
| 5,971,983 | A | | 10/1999 | Lesh |
| 6,542,781 | B1 | | 4/2003 | Koblish et al. |
| 6,623,449 | B2 | | 9/2003 | Paskar |
| 6,758,830 | B1 | * | 7/2004 | Schaer et al. ............... 604/95.04 |
| 2001/0056260 | A1 | | 12/2001 | Grimes et al. |
| 2002/0188276 | A1 | * | 12/2002 | Evans et al. .................. 604/509 |
| 2004/0116941 | A1 | * | 6/2004 | Reynolds et al. ............ 606/128 |
| 2006/0184089 | A1 | | 8/2006 | Makower et al. |
| 2006/0252993 | A1 | * | 11/2006 | Freed et al. .................. 600/146 |

* cited by examiner

Primary Examiner — Victor Nguyen
Assistant Examiner — Kevin Everage
(74) Attorney, Agent, or Firm — Brinks Gilson & Lione

(57) ABSTRACT

A device for providing access to a treatment site within the body of a patient includes a tubular member having a first, generally elongated configuration for introduction into the body of the patient, and deployable therein to a second configuration. The second configuration includes an axially displaced segment along the distal portion of the tubular member. The tubular member includes a side port oriented along the axially displaced segment, and further includes a lumen communicating with the side port. The lumen and side port are sized for passage therethrough of an interventional device for delivery to the treatment site.

11 Claims, 6 Drawing Sheets

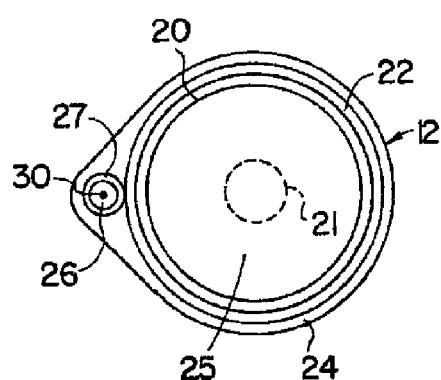
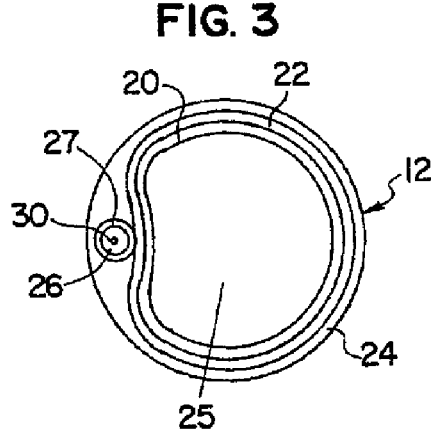
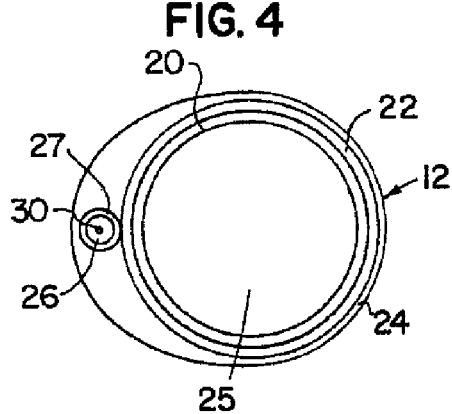
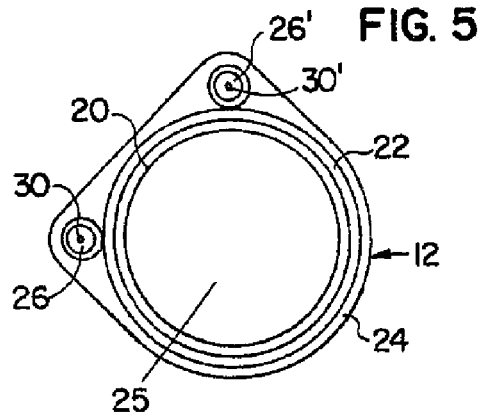
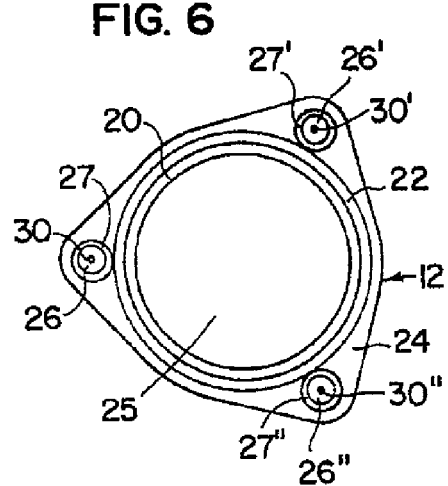
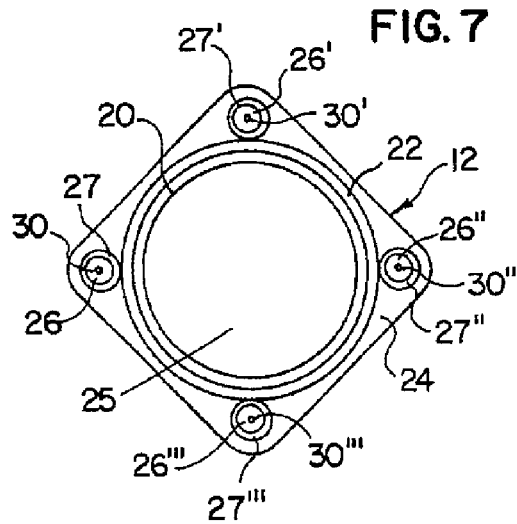

ACCESS DEVICE

RELATED APPLICATION

The present patent document claims the benefit of the filing date under 35 U.S.C. §119(e) of Provisional U.S. Patent Application Ser. No. 60/856,149, filed Nov. 2, 2006, which is hereby incorporated by reference.

BACKGROUND

1. Technical Field

The present invention relates to a device for providing access to a treatment site within the body of a patient, and more particularly, to a device for providing access to a treatment site within a branched vessel, such as a renal artery, deep within the vasculature to enable placement of an interventional device.

2. Background Information

In the medical arts, it is frequently desirable to deliver a medical interventional device, such as a stent, to a remote treatment site deep within the vasculature of a patient. In order to access such a remote site, it may be necessary to thread or otherwise insert one or more introducer and/or dilational devices through increasingly narrow, branched vessels before reaching the target site. The introducer device, such as a sheath, through which the medical interventional device is passed, is typically inserted percutaneously by well-known means. One common procedure is the Seldinger percutaneous access technique, wherein an introducer sheath is inserted over a previously-positioned wire guide. In many cases, the introducer sheath may have a pre-curved tip at the distal end and a hemostasis valve on the proximal end. Other well-known desirable features of an introducer sheath may include an atraumatic tip, torqueable construction, radiopaque markers and/or a lubricious coating.

Achieving access to a target site within the vasculature of the patient for delivery of an interventional device often does not cause undue difficulty for the medical professional. However, on other occasions access has proven to be problematic. Typically, such problems arise when the medical interventional device must be implanted at a remote site deep within the vasculature, often requiring access to one or more vessels that branch off from a major vessel at extreme angles. Other potential problems that may be encountered include imprecise control of the introducer device due to an insecure purchase of the sheath, as well as a difficulty in determining the location and position of one or more side branches, such as, for example, the renal arteries. In addition, sizing the affected vessels/lesions may be problematic.

It is desired to provide a device for providing access to remote target sites that overcomes the disadvantages encountered with conventional devices.

BRIEF SUMMARY

The present invention addresses the problems of the prior art. In one form thereof, the invention comprises a device for providing access to a treatment site within the body of a patient. The device includes a tubular member having a proximal portion and a distal portion. The tubular member has a first, generally elongated configuration for introduction into the body of the patient, and is deployable therein to a second configuration. The second configuration includes an axially displaced segment along the tubular member distal portion. The tubular member includes a side port oriented along the axially displaced segment, and further includes a lumen communicating with the side port. The lumen and side port are sized for passage therethrough of an interventional device for delivery to the treatment site.

In another form thereof, the invention comprises a device for use in providing access to a treatment site of a patient. The device comprises a tubular member having a proximal portion and a distal portion. A length of the distal portion is capable of axial displacement into a generally curved configuration. The tubular member further includes a side port at the displaced portion. An actuator is provided for controlling the displacement of the distal portion length. An actuating wire is also provided. A first portion of the wire is engaged with the actuator, and a second portion of the wire is engaged with the tubular member. The actuator is operable for creating a tension in the wire. The distal portion length is axially displaceable into the generally curved configuration responsive to the tension.

In yet another form thereof the invention comprises a system for providing access to a treatment site within the body of a patient. The system includes a tubular member having a first, generally elongated configuration for introduction into the body of the patient, and being deployable therein to a second configuration. The second configuration includes an axially displaced segment along the distal portion of the tubular member. The tubular member includes a side port oriented along the axially displaced segment, and further includes a lumen communicating with the side port. A delivery catheter for a medical intervention device is sized for passage through the lumen and side port, and for accessing the treatment site.

BRIEF DESCRIPTION OF THE DRAWINGS

FIG. 2 is a sectional view of the access device of FIG. 1, taken along line 2-2;

FIGS. 3-7 illustrate cross-sectional views of alternative embodiments of the tubular member of an access device according to the present invention;

DETAILED DESCRIPTION OF THE DRAWINGS AND THE PRESENTLY PREFERRED EMBODIMENTS

Figure 1:
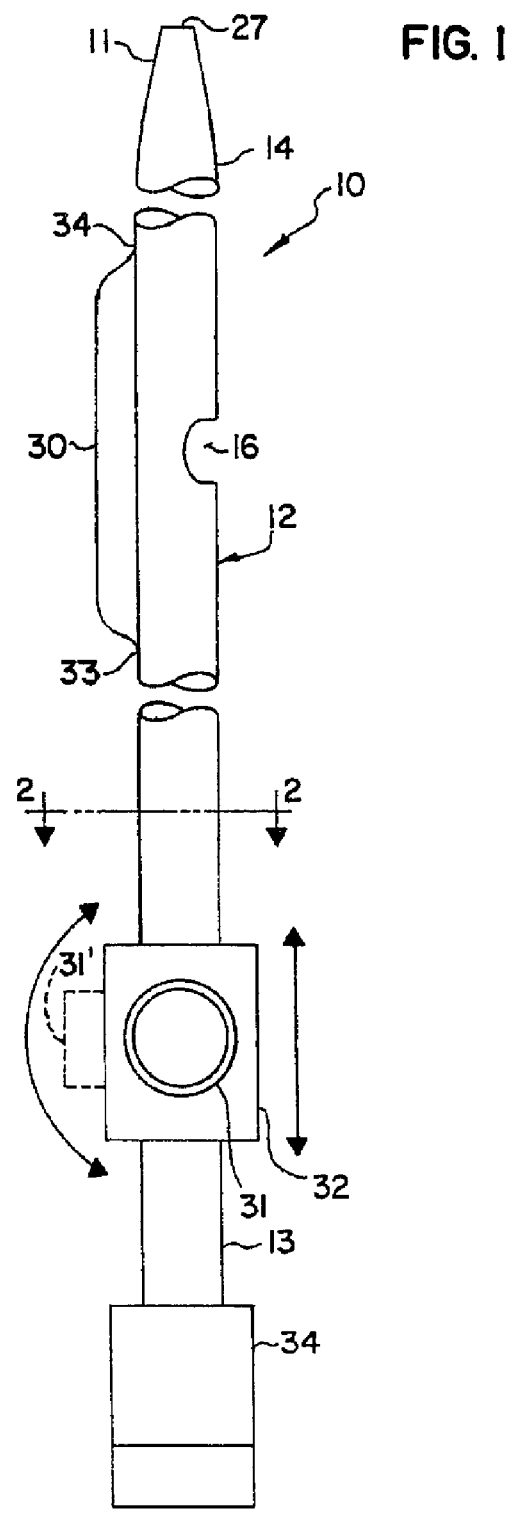
FIG. 1 is a side view of one embodiment of an access device of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive access device, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient during use.

FIG. 1 illustrates a side view of an access device 10 according to one embodiment of the present invention. As shown, access device 10 comprises an elongated tubular body 12 having a proximal portion 13 and a distal portion 14. FIG. 2 illustrates a sectional view of tubular body 12 taken at line 2-2 of FIG. 1. As shown in FIG. 2, tubular body 12 comprises a layered structure having an inner liner 20, a reinforcing member 22, and a polymeric outer layer 24.

Preferably, inner liner 20 comprises a lubricious polymer, such as a fluorocarbon. PTFE is one non-limiting example of a lubricious polymer suitable for use as an inner liner in access device 10. Preferably, the reinforcing member 22 comprises a coil, and more preferably, a flat wire coil formed, e.g. of stainless steel. Alternatively, other known reinforcing members, such as a braid or a coil formed from compositions other than flat wire, may be substituted. Various 30 metals, metal alloys and other materials suitable for use as reinforcements are well known in the art, and may be used herein. The outer layer 24 is typically formed of a polymeric composition, such as a polyether block amide or a nylon. Polymeric materials suitable for such use are well known in the art, and those skilled in the art will appreciate that numerous such materials may be substituted for those named herein. The outer polymeric layer 24 need not be formed from the same composition along its entire length, and may comprise more than one durometer along its length. Additionally, outer layer 24 may be coated with a hydrophilic composition if desired.

Tubular bodies having a layered structure similar to that of tubular body 12 are well known in the medical arts, and are commercially available, e.g., from Cook Incorporated, of Bloomington, Ind. Those skilled in the art will appreciate that other known tubular structures suitable for the purposes described herein may be substituted for the layered structure shown and described, which structures may, or may not, have a layered structure and/or a reinforcement as described.

Preferably, tubular body 12 is constructed in well known fashion, such as by a heat set operation, to take on a permanent curve for facilitating threading of the access device through the vascular system to the target site. Processes for heat setting of catheters, sheaths, and other tubular bodies for such purposes are well known, and those skilled in the art are readily able to heat set a tubular body to a desired curvature. Typically, a tubular body that is curved as described herein is straightened during introduction by insertion of a removable inner member, such as obturator 21 shown in FIG. 2, through the main lumen of the tube, which inner member is removed at the time that the curvature is desired for facilitating positioning of the device.

As further shown in the preferred embodiment of FIG. 2, tubular body 12 comprises dual lumens 25, 26. The large diameter main lumen 25 is sized to enable passage therethrough of a conventional delivery catheter that carries the medical interventional device, such as an expandable stent, intended for placement at the target site. Although the interventional device is described herein for convenience as a stent, this is merely one example of a type of interventional device that can be delivered to the target site, and other known interventional devices may likewise be inserted utilizing the inventive device. When the interventional device is a balloon expandable stent, the delivery catheter includes an inflatable balloon for expanding the stent at the target site in well-known fashion. When the stent is formed of a self-expandable composition, such as the nickel-titanium alloy nitinol, the delivery catheter typically includes a removable shield that maintains the stent in the compressed position until the target area is reached, at which time the shield is removed and the stent self-expands within the vessel. Delivery catheters suitable for delivery of expandable interventional devices are well known in the art, and further description of them is not necessary for an understanding of the features of the present invention. Access device 10 may also include a conventional hub 34 disposed at the proximal end of the device. Hub 34 communicates with main lumen 25, and is sized and shaped to enable passage therethrough of the delivery catheter in well known fashion.

Smaller lumen 26 is disposed generally parallel to main lumen 25. In the embodiment shown, lumen 26 is formed through a radially extending protrusion of outer layer 24. Preferably, a lubricious liner 27, such as PTFE, lines the internal surface of lumen 26. Lumen 26 is sized to enable passage therethrough of an actuating wire 30. As illustrated, actuating wire 30 extends through lumen 26 until it reaches outlet port 33 disposed along a distal portion of tubular body 12. As shown in FIG. 1, wire 30 exits tubular body 12, and lumen 26, at exit port 33, and extends parallel to tubular body 12 external of that body for a defined length. Wire 30 then reenters lumen 26 of tubular body 12 through inlet port 34. Unlike lumen 25, which extends through open distal end 27 of tubular body 12, the distal end of smaller lumen 26 is closed off by the tapered distal end 11 of tubular body 12. The extreme distal end of wire 30 is attached to body 12 at said closed off, or terminal, point by conventional means, such as adhesion.

In the embodiment shown, access device 10 includes an actuator 32 disposed at the proximal end of tubular member 12. Actuator 32 may comprise a conventional structure, such as control wheel 31, around which the proximal end of wire 30 may be tied or otherwise affixed. Upon rotation of control wheel 31 in a desired direction, wire 30 winds (or unwinds). When wire 30 winds in the desired direction, tension is exerted on the wire, and thus on tubular body 12, such that a segment of the tubular member is axially displaced, or deflected, e.g., in the manner shown in FIG. 8. Those skilled in the art will appreciate that other known actuating mechanisms, such as a knob or a lever, may be substituted for the control wheel described to create tension on the wire and to cause axial displacement of the tubular body as described. The access device further includes a side port 16 sized and shaped to enable passage therethrough of the delivery catheter or like device, in a manner to be described.

The wire 30 need not necessarily exit the tubular body as shown in FIG. 1 in order to accomplish the deflection. Rather, as one possible alternative to this configuration, the wire can remain in the lumen, and deflection may be accomplished by foreshortening one side of the sheath. Those skilled in the art will appreciate that there are other ways in which deflection of the tubular body may be accomplished, which methods are considered within the scope of the invention.

Although FIG. 2 illustrates one preferred cross-sectional configuration of tubular member 12, the arrangement illustrated therein is merely one preferred example, and other arrangements may be substituted. FIGS. 3-7 illustrate additional non-limiting examples of cross-sectional configurations of tubular member 12. Features common to each of the alternatives of FIGS. 2-7, such as the tubular body 12, inner liner 20, reinforcing member 22, outer layer 24, main lumen 25, wire lumen 26, wire lumen liner 27, and wire 30 have common reference numerals in each figure.

FIGS. 3 and 4 illustrate alternative configurations for an embodiment having a single wire lumen 26. In FIG. 3, the outer profile of tubular member 12 maintains more of a circular shape than the design of FIG. 2, although a diameter of main lumen 25 is compressed. In FIG. 4, the outer profile of tubular member 12 retains a more rounded configuration, and the profile of main lumen 25 also maintains a round configuration.

FIGS. 5-7 illustrate configurations having more than one wire lumen. In FIG. 5, a second wire lumen 26' is provided and a second control wire 30' extends therethrough. In FIG. 6, second and third wire lumens 26' and 26" are provided, along with second and third control wires 30' and 30". In FIG. 7, second, third and fourth wire lumens 26', 26" and 26''' are provided, along with second, third and fourth control wires 30', 30" and 30'''. Utilizing more than one control wire enables the physician to manipulate the access device in more than one plane, rather than in the generally back and forth movement available with a single wire. In this event, multiple actuating mechanisms, such as multiple control wheels 31, may be provided, in a manner such that a separate control wheel may be used to create tension in each such wire if desired. As shown in FIG. 1, a second control wheel 31' may be provided, for example, at an adjoining or opposite face of actuator 32 from control wheel 31.

Figure 8:
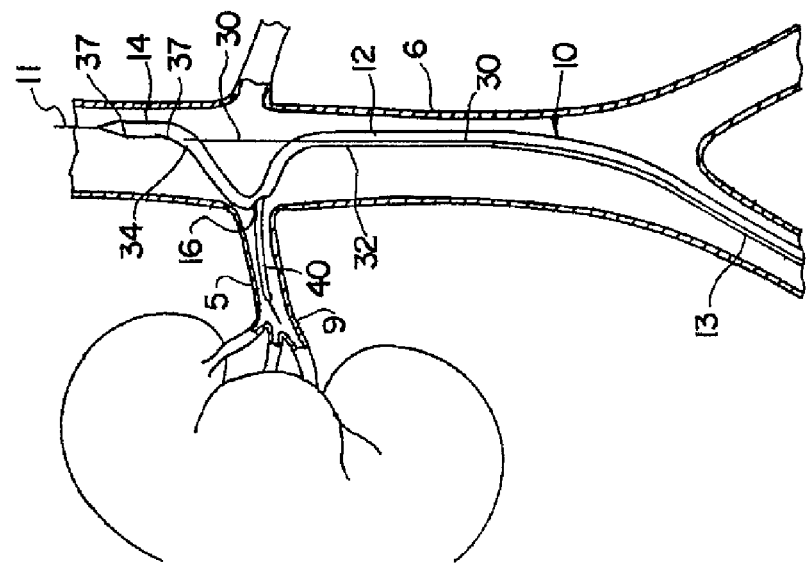
FIG. 8 illustrates one example of the use of an access device according to the present invention for accessing a branched artery.

FIG. 8 illustrates one example of the use of access device 10 for accessing a branched artery, in this case a renal artery 5. Initially, access is obtained through a suitable artery, such as the femoral artery, by conventional means such as the well-known Seldinger technique. A wire guide 11 is inserted into the femoral artery, and threaded through the aorta 6 beyond the targeted branched artery 5. An introducer device may be utilized, in which case the access device may be passed through the introducer device in a manner such that distal portion 14 of the access device extends beyond the branched artery 5. Alternatively, access device 10 may be utilized as an introducer device, thereby eliminating the necessity of employing a separate introducer. Preferably, access device 10 is provided with one or more radiopaque markers 37 for determining the position of the distal end of the access device. Instead of, or in addition, to, using radiopaque markers 27, a contrast dye can also be injected to assist in viewing the target area. When properly positioned, port 16 of access device 10 is substantially aligned with branched artery 5.

Actuator 32, such as the control wheel 31 shown in FIG. 1, is then actuated to retract wire 30 in the proximal direction (to the bottom of the figure in the orientation of FIG. 8), thereby causing a distal portion of sheath body 12 to be axially displaced, or deflected, in the manner shown. When the tubular body has been heat set as described, deflection may be accomplished by a combination of the axially displacement responsive to the tension in the wire as described, and the curvature of the tube resulting from the removal of the obturator. This combination of features advantageously enables the operator to very precisely form a displacement at an intended site.

When tubular member 12 is axially displaced as described, port 16 is positioned to provide communication with artery 5, as shown in FIG. 8. Preferably, a wire guide 9 is initially manipulated through the side port and past the target site or lesion. A delivery catheter, such as catheter 40, may then be threaded through tubular body 12 over wire guide 9, until it reaches side port 16. At this time, delivery catheter 40 may be manipulated in known fashion such that it is directed through port 16 and into artery 5. Delivery catheter 40 carries an interventional device, such as a balloon expandable or a self-expandable stent, for deployment in the targeted artery by conventional means. Following deployment, the delivery catheter is retracted through access device 10, and the control wheel may be rotated in the opposite direction to enable access device 10 to resume the position shown in FIG. 1. The access device may then be withdrawn by reversing the steps by which it was introduced.

Figure 9:
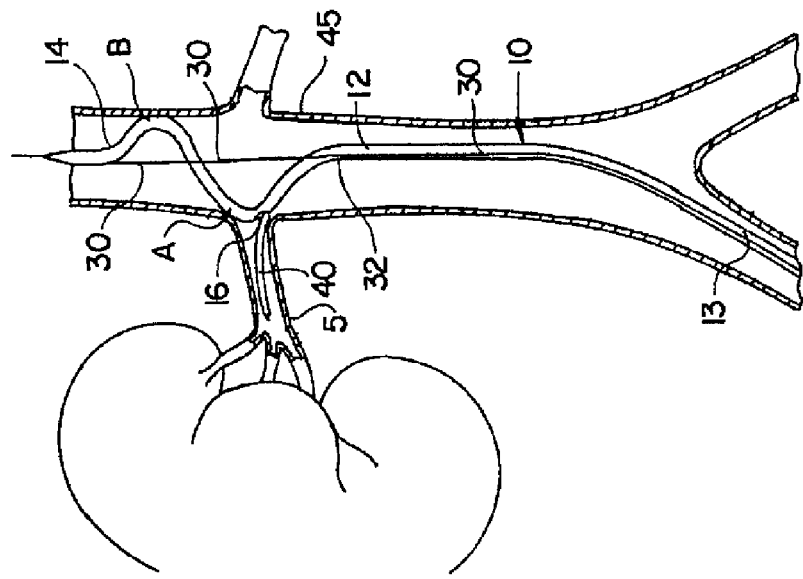
FIGS. 9 and 10 illustrate alternative embodiments of an access device used to access a branched artery.

FIG. 9 illustrates another example of the use of an access device 10 for accessing branched artery 5. In this embodiment, retraction of the wire 30, and withdrawal of the obturator, if present, causes a double bend along the length of the distal portion of sheath body 12. Port 16 is disposed along anterior bend A, and is aligned with artery 5 in the same manner as the example of FIG. 8. Posterior bend B exerts a force on the wall of aorta 45, thus pushing anterior bend A in the direction of artery 5 as shown. In this embodiment, the access device 10 may be provided with more than one set of inlet and outlet ports to enable the actuation wire to exit and re-enter the tubular body. This may provide for enhanced control of the actuator.

Figure 10:
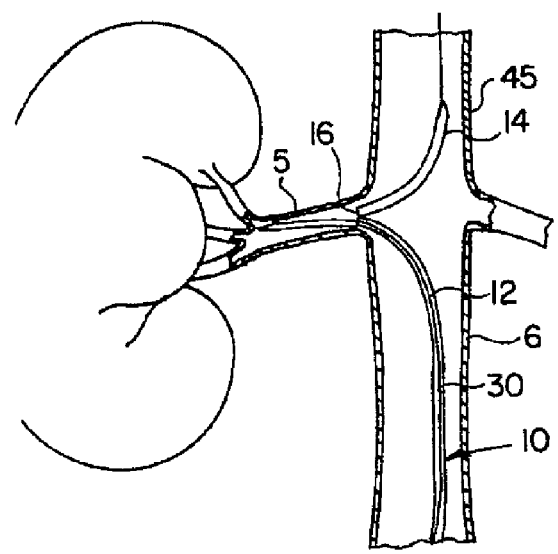

FIG. 10 illustrates yet another embodiment showing the use of an access device for providing access to branched artery 5. In this embodiment, retraction of wire 30 causes tubular body 12 to deflect more sharply at port 16, and the remaining material bridging port 16 acts as a hinge. With this configuration, port 16 readily accesses branched artery 5, and distal portion 14 of tubular body 12 is made to bear against opposing wall 45 of aorta 6.

As illustrated above, the access device 10 includes a port 16 through which the delivery catheter may be passed to access the targeted site. Although illustrated in FIG. 1 as a generally circular cut-out from tubular body 12, port 16 may have alternative configurations. FIGS. 11-17 illustrate numerous possible arrangements of the port, as well as the tubular body in the vicinity of the port.

Figure 11:
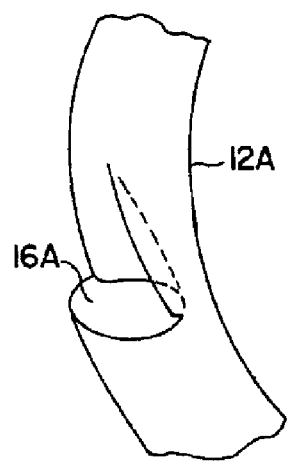
FIG. 11-17 illustrate alternative embodiments of access devices showing different designs of the side port.

FIG. 11 illustrates an arrangement wherein port 16A is formed in the nature of an "exit-ramp" that is formed in tubular body 12A. The ramp may be formed by making a generally perpendicular cut approximately one-half of the way through the tubular body, and placing a mandrel into opposing ends of the tubular body until the area of the desired ramp is reached. The immediate wall may then be deflected in an inward direction and heat set to maintain the ramp configuration.

Figure 12:
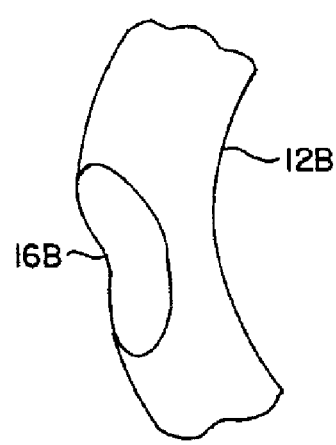
Figure 13:
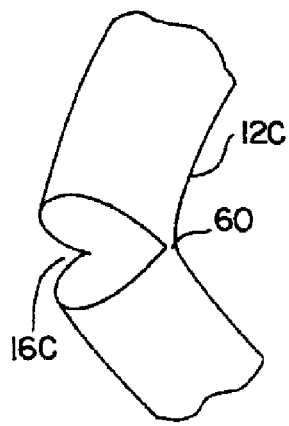

FIG. 12 illustrates an arrangement wherein port 16B is skived from the tubular body 12B by well-known means. FIG. 13 illustrates an arrangement wherein port 16C is formed as a notch cut into tubular body 12C. This arrangement results in the formation of a hinge 60 opposite port 16C. The presence of the hinge facilitates the flexing, or bending, of tubular body 12C at the access site.

Figure 14:
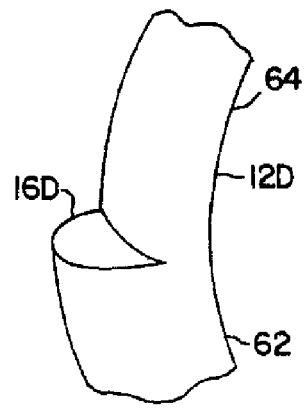

FIG. 14 illustrates an arrangement wherein tubular body 12D has two diameters. A proximal portion 62 has a larger diameter and a distal portion 64 has a smaller diameter. The presence of the smaller diameter distal portion enables the device to access arterial sections that may be difficult, if not impossible, to access with the larger diameter portion. Tubular devices having dual diameters suitable for use herein are commercially available, e.g., from Cook Incorporated, of Bloomington, Ind., and are sold as FLEXOR® introducers. The diameters of the respective larger diameter and smaller diameter sections may be varied in accordance with the intended used of the access device. When used to access the renal arteries, the proximal diameter may be, e.g., 5, 6 or 7 French, and the corresponding distal diameter may be 4, 5 or 6 French, respectively.

Figure 15:
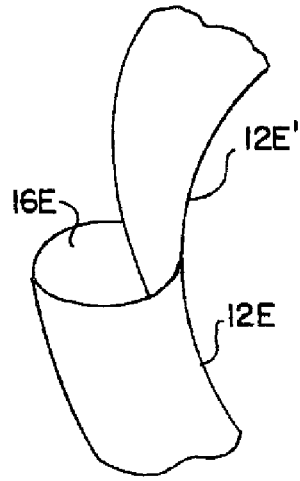

FIG. 15 illustrates an arrangement wherein two sheaths 12E and 12E' are joined in a manner such that port 16E is formed at their juncture. Sheaths 12E and 12E' need not have the same diameter, and need not be formed of the same composition. For example, sheath 12E can comprise a layered structure, such as a PTFE inner liner, a flat wire coil reinforcement, and a polyamide block ether outer layer, as described previously. Adjoining sheath 16E may be a smaller diameter tube, and need not include a coil and/or multiple polymeric layers. In the arrangement of FIG. 15, the proximal portion may desirably be torqueable, and have a lumen sufficiently large to enable passage therethrough of an interventional device. The lumen of the distal portion, on the other hand, need only be large enough for passage of a wire guide, and optionally, to enable the portion to have sufficient structural integrity to bear against an opposing artery wall.

Figure 16:
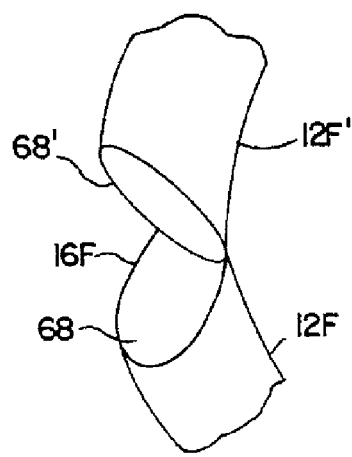
Figure 17:
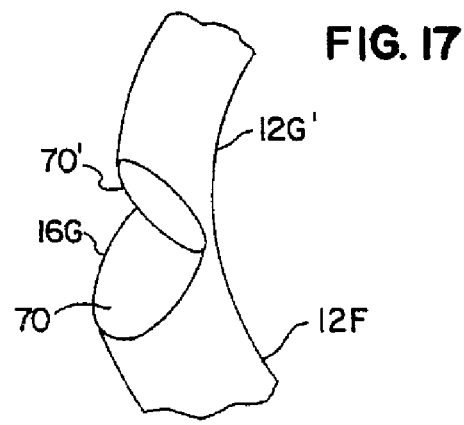

FIG. 16 illustrates an arrangement wherein two sheaths 12F, 12F' are joined, in a manner similar to that of FIG. 16 to define port 16F. In this embodiment, sheaths 12F, 12F' are provided with respective beveled ends 68, 68'. One of the beveled ends, in this case end 68', may be inserted partially into the other beveled end 68, thereby providing an overlap in the two portions that may be bonded together. FIG. 17 illustrates an arrangement similar to that of FIG. 16, wherein sheaths 12G, 12G' are joined to define port 16G. Once again, sheaths 12G, 12G' are provided with respective beveled ends 70, 70'. Since the distal portion has a smaller diameter than the proximal portion, a portion of the beveled end of the distal portion may be readily inserted into the beveled end of the proximal portion, thereby providing an overlap in the two portions that may be bonded together.

Figure 18:
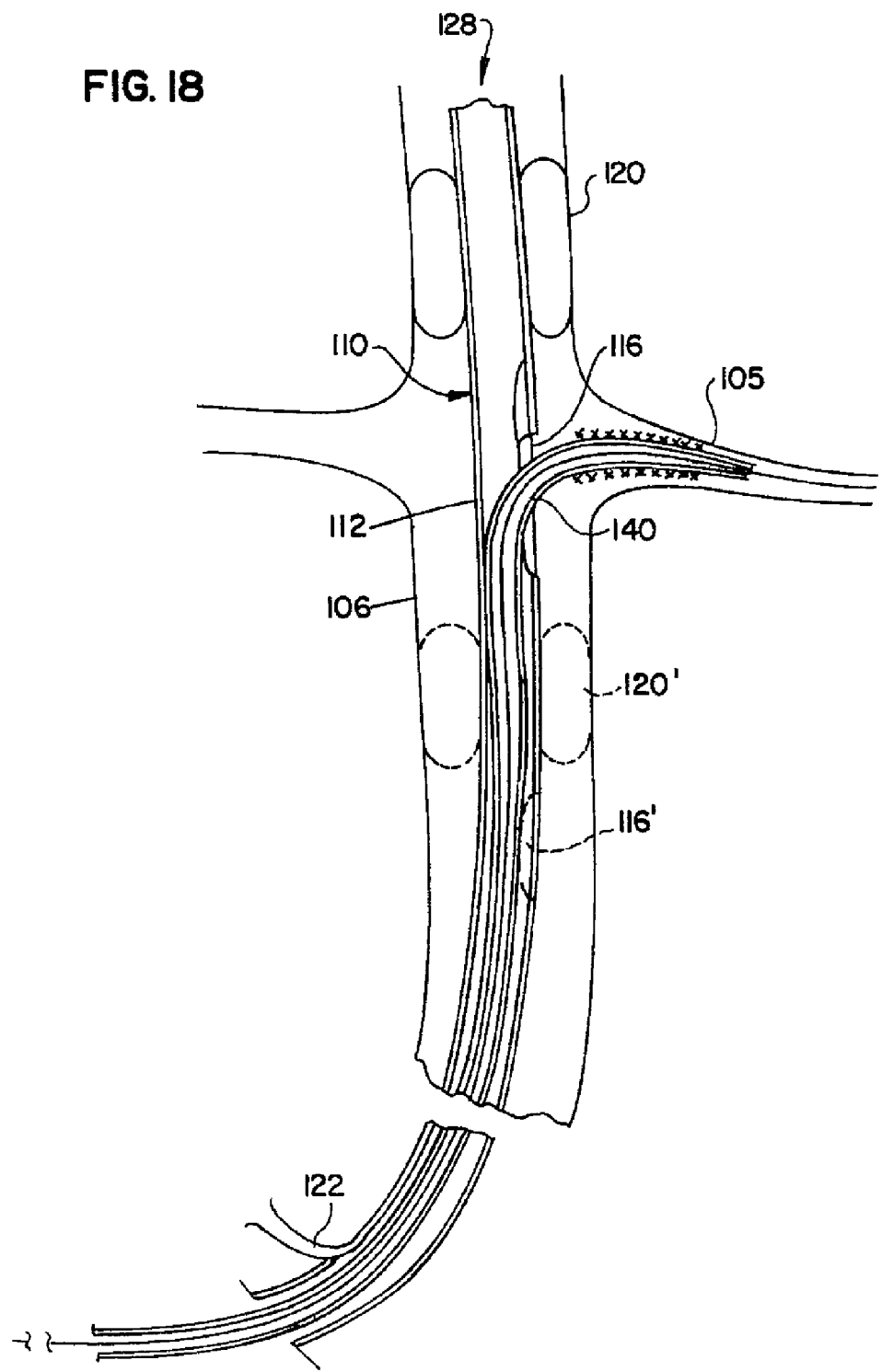
FIG. 18 illustrates another alternative of an access device utilizing an anchoring balloon.

FIG. 18 illustrates another embodiment of an access device 110 according to the present invention. With the exception of the features specifically described below, the remainder of access device 110 may be similar to any of the features already described herein. Access device 110 is shown positioned in the aorta 106 of a patient. A delivery catheter 140 is threaded through tubular body 112 of access device 110, and passes through port 116 into the branched renal artery 105. A balloon 120 is provided distal to the renal branching. Balloon 120 is sized such that upon inflation of the balloon, access device 110 is anchored by the balloon in the aorta. This arrangement provides additional anchoring of the access device, so that it cannot be easily forced in the proximal direction in response to advancement of the interventional device in the distal direction. To accomplish inflation, tubular body 112 includes an inflation lumen 122 for transmitting an inflation fluid through tubular body 112 to the interior space of balloon 120. An opening 128 of tubular body 112 is provided at the distal end of the body to permit passage of blood through the aorta.

A still further alternative is illustrated by the broken lines in FIG. 18. In this alternative, a second anchoring balloon 120' (shown in phantom) is provided. When present, this balloon may provide additional anchoring of the access device 100. In addition, another side port 116' can be provided proximal of balloon 120'. During venous access, a clot may become dislodged, which dislodged clot will tend to travel downstream. Providing the dual balloons as illustrated provides a bypass that isolates the treatment area, and enables the clots can be readily removed, e.g., by aspiration.

Although the preferred embodiments of the invention have been described, other variations are possible, and are within the scope of the invention. For example, in some instances in may be possible to utilize solely a heat set tube to accomplish the desired axial deflection, and the actuating member and/or wire need not be present. Similarly, axial deflection may alternatively be accomplished by use of a shape memory composition, such as nitinol. As a still further alternative, deflection may be achieved by use of an actuator as described, and heat setting or otherwise providing a memory in the tubular member may not always be necessary. Those skilled in the art will appreciate that there are other ways to actively displace, or deflect, a specific portion of a tubular member into a specific configuration, all of which are considered within the scope of the invention.

It is therefore intended that the foregoing detailed description be regarded as illustrative rather than limiting, and that it be understood that it is the following claims, including all equivalents, that are intended to define the spirit and scope of this invention.

The invention claimed is:

1. A device for providing access to a treatment site within the body of a patient, comprising:
   a tubular member having a proximal portion and a distal portion, said distal portion extending to a distal end, said tubular member having a first, generally elongated configuration for introduction into a first vessel in the body of the patient, and being deployable therein to a second configuration wherein said proximal portion and said distal end remain at least substantially in the generally elongated configuration, and a segment of said distal portion proximal of said distal end is axially displaced from said generally elongated configuration of said proximal portion and said distal end, said tubular member comprising a side port disposed on said axially displaced segment, said tubular member further comprising a first lumen communicating with said side port, said axially displaced segment and said side port alignable in said first vessel for passage therethrough of an interventional device for delivery to said treatment site in a second vessel, said second vessel branched from said first vessel; and
   an actuating wire extending through a second lumen of said tubular member, said first and second lumens being separated from each other, said second lumen and said actuating wire extending along said tubular member to a first port adjacent a proximal side of said axially displaced segment, said actuating wire exiting said second lumen and said tubular member through said first port and extending external of said tubular member and parallel therewith, said actuating wire reentering said second lumen and said tubular member through a second port adjacent a distal side of said axially displaced segment, said actuating wire extending through said second lumen to said distal end of said tubular body, said second lumen being closed off adjacent said distal end of said tubular body, and a distal end of said actuating wire being attached to said tubular body adjacent said distal end of said tubular body;
   wherein said segment of said tubular body is axially displaced in response to tension exerted on said actuating wire.

2. The device of claim 1, further comprising:
   an actuator engaged with said actuating wire for controlling a deployment of said tubular member to said second configuration.

3. The device of claim 2, wherein said actuator comprises a control wheel, and wherein said tension is created in said actuating wire by rotating said control wheel.

4. The device of claim 1, wherein said tubular member comprises a generally lubricious inner liner defining said first lumen, a reinforcing member generally surrounding said inner liner, and an outer layer generally surrounding said inner liner and said reinforcing member.

5. The device of claim 4, wherein said generally lubricious inner liner comprises PTFE, said reinforcing member comprises a coil, and said outer layer comprises at least one of a polyether block amide and nylon.

6. The device of claim 4, further comprising a generally lubricous liner defining said second lumen, and wherein said second lumen is axially disposed through a length of said outer layer.

7. The device of claim 1, wherein said second lumen further comprises at least second and third lumens, and wherein a respective actuating wire extends through at least a portion of each of said second and third lumens.

8. The device of claim 1, further comprising at least one marker along a length of said tubular member for providing a visual identification of a length of said tubular member.

9. A system for providing access to a treatment site within a branched vessel in the body of a patient, comprising:

a tubular member having a proximal portion and a distal portion, said tubular member extending to a distal end and having a first, generally elongated configuration for introduction into a first vessel in the body of the patient, and being deployable therein to a second configuration, said second configuration including a curved segment along said tubular member distal portion relative to a proximal of said distal end of said tubular member in said generally elongated configuration, said tubular member comprising a side port oriented along said curved segment, said tubular member further comprising a first lumen communicating with said side port, and comprising a second lumen separated from said first lumen, said side port positioned along said curved segment for establishing communication therethrough between said first lumen and said branched vessel, said tubular member further comprising an outlet port and an inlet port communicating with said second lumen, said curved segment having said side port positioned therealong being substantially intermediate said outlet port and said inlet port along a length of said tubular member;

an actuator engaged with said tubular member for controlling a deployment of said tubular member to said second configuration;

an actuating wire extending through at least a portion of said second lumen, said actuating wire positioned such that a segment of said wire exits said second lumen at said outlet port and reenters said second lumen at said inlet port, said actuating wire extending external of said tubular member and parallel therewith along said curved segment of said tubular member, said actuating wire extending through said second lumen to said distal end of said tubular body, said second lumen being closed off adjacent said distal end of said tubular body, and a distal end of said actuating wire being attached to said tubular body adjacent said distal end of said tubular body, a proximal portion of said actuating wire engaged with said actuator, said actuator being operable for creating a tension in said actuating wire, said curved segment being axially displaceable from said generally elongated configuration responsive to said tension; and a delivery catheter sized for passage through said first lumen and said side port, and for accessing said treatment site in said branched vessel when said tubular member is in said second configuration.

10. The device of claim 1, wherein said axially displaced segment comprises a generally curved configuration relative to said tubular member generally elongated configuration, and wherein said side port is disposed along said generally curved configuration.

11. The device of claim 10, wherein said side port is disposed substantially along a mid-point of said generally curved configuration.

* * * * *